United States Patent [19]

Strandberg et al.

[11] Patent Number: 4,757,815
[45] Date of Patent: Jul. 19, 1988

[54] HEART PACEMAKER

[75] Inventors: Hans Strandberg, Sundbyberg; Sven-Erik Hedberg, Kungsängen; Martin Obel, Danderyd, all of Sweden

[73] Assignee: Siemens Aktiengesellschaft, Berlin and Munich, Fed. Rep. of Germany

[21] Appl. No.: 942,719

[22] Filed: Dec. 17, 1986

[30] Foreign Application Priority Data

Dec. 20, 1985 [DE] Fed. Rep. of Germany ....... 3545359

[51] Int. Cl.$^4$ .............................................. A61N 1/36
[52] U.S. Cl. .............................. 128/419 PG; 128/716; 128/671
[58] Field of Search ................. 128/419 PG, 716, 671

[56] References Cited

U.S. PATENT DOCUMENTS

| 3,593,718 | 7/1971 | Krasner | 128/419 |
|---|---|---|---|
| 4,303,075 | 12/1981 | Heilman et al. | 128/419 PG |
| 4,365,636 | 12/1982 | Barker | 128/716 |
| 4,428,378 | 1/1984 | Anderson et al. | 128/419 PG |
| 4,596,251 | 6/1986 | Plicchi et al. | 128/419 PG |

FOREIGN PATENT DOCUMENTS 0089014 9/1983 European Pat. Off. ........... 419 PG/

OTHER PUBLICATIONS

"Valsalva-Induced Variations in the Intracardiac Signal", Rosenqvist et al, PACE, vol. 8, Nov.-Dec. 1985, pp. 856-861.
"Variations of the Intraatrial Potential in Patients with a DDD Pacemaker," Langenfeld et al, Cardiac Pacing & Electrophysiology, Jun. 7-11, 1987, pp. 185-189.
"Relationship Between Changes in R Wave Voltage & Cardiac Volumes. A Vectorcardiographic Study During Hemodialysis," Vitolo et al, J. Electrocardiology vol. 20(2), 1987, pp. 138-146.

Primary Examiner—William E. Kamm
Assistant Examiner—Timothy Keegan
Attorney, Agent, or Firm—Hill, Van Santen, Steadman & Simpson

[57] ABSTRACT

A heart pacemaker has a pulse generator and circuitry for measuring a respiration signal of the user and a control unit for controlling the pulse generator by changing the pulse repetition rate dependent on the respiration signal. A heart action detector is provided for acquiring heart action signals and the respiration signal measuring circuitry includes detectors for measuring the amplitude fluctuations in the heart action signal and supplying those fluctuations to the control unit.

5 Claims, 1 Drawing Sheet

HEART PACEMAKER

BACKGROUND OF THE INVENTION

1. Field of the Invention

The present invention relates to heart pacemakers, and in particular to heart pacemakers which vary the output pulse rate based on respiration activity of the user.

2. Description of the Prior Art

Heart pacemakers are known which employ a respiration signal obtained from the user of the pacemaker to vary the repetition rate of the pulses generated by the pacemaker. Such pacemakers are described, for example, in U.S. Pat. No. 3,593,718 and in European patent application No. 00 89 014. These known heart pacemakers use an impedance pneumograph for acquiring a respiration signal. Such an impedance pneumograph requires additional electrodes and energy for impedance measurement.

SUMMARY OF THE INVENTION

It is an object of the present invention to provide a heart pacemaker which varies the output pulse repetition rate in dependence upon a respiration signal from the pacemaker user in a simple manner with low energy consumption.

In accordance with the principles of the present invention, the above object is achieved in a pacemaker having a pulse generator, a respiration signal measuring means, and control means for controlling the pulse generator by modifying the pulse repetition rate thereof dependent on the respiration signal. The pacemaker has a heart action detector for acquiring a heart action signal, and the respiration signal measuring means includes means for determining amplitude fluctuations in the heart action signal and supplying a signal corresponding to those fluctuations to the control unit as the respiration signal.

The respiration signal in the pacemaker disclosed herein can thus be directly acquired from fluctuations of the heart action signal. An additional current for making an impedance measurement is thus not required and no extra electrode is needed. The pacemaker is thus technically simpler to construct and consumes less energy to operate.

DESCRIPTION OF THE PREFERRED EMBODIMENTS

Figure 1:
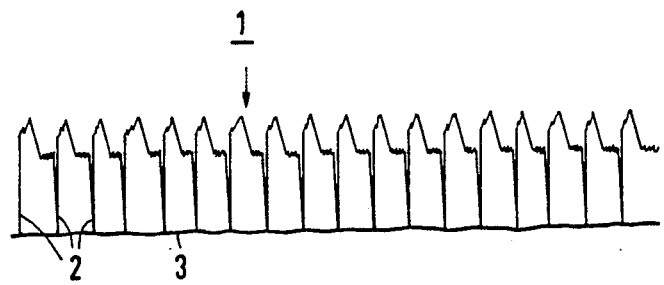
FIG. 1 is a schematic illustration of heart action signals and their amplitude fluctuations from which a respiration signal can be derived.

A series of heart action signals 1 is shown in FIG. 1 which are acquired by a heart pacemaker in a conventional manner, such as by means of a QRS detector. The amplitudes 2 (R waves) thereof are subject to fluctuations caused by the respiration cycle of the user of the heart pacemaker. The envelope for all such fluctuations is referenced 3 in FIG. 1. In accordance with the principles of the present invention, this envelope corresponds to the respiration signal.

Figure 2:
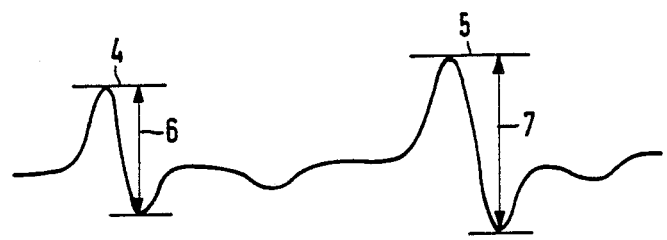
FIG. 2 is an enlarged portions of successive heart action signals of the type shown in FIG. 1 and illustrates the measuring principle employed by the pacemaker disclosed herein.

Two successive QRS complexes 4 and 5 are shown enlarged in FIG. 2 having different amplitudes. As shown in FIG. 2, a measurement is undertaken for each complex from the most positive point to the most negative point of the R wave, with the respective distances 6 and 7 between the peak values being the measure of the respiration signal used in the present invention.

Figure 3:
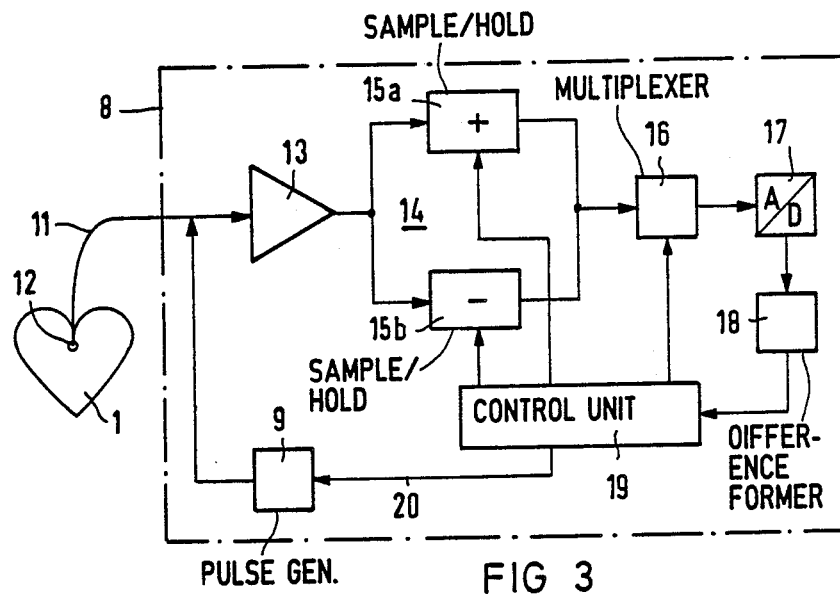
FIG. 3 is a schematic block circuit diagram of a heart pacemaker constructed in accordance with the principles of the present invention.

A schematic circuit diagram for a heart pacemaker for operating based on the measurement principles described above is shown in FIG. 3. The pacemaker is encapsulated in a housing 8 and comprises a pulse generator 9 for generating heart pacing pulses which are conducted to a heart 10 via an electrode line 11 having an electrode tip 12 introduced in the heart 10. The pacemaker further includes an amplifier 13 for the incoming heart action signals acquired by the electrode line 11. The amplifier 13 is followed by a peak sensing means 14 for QRS complexes including a first sample/hold element 15a for positive peaks and a second sample/hold element 15b for negative peaks.

The acquired peak values are supplied through a multiplexer 16 and an analog-to-digital converter 17 to a difference former 18. The difference former 18 forms a signal corresponding to the differences between the acquired positive and negative peaks for each QRS complex. The output signal of the difference former 18 is supplied to a control unit 19 as a respiration signal for the heart pacemaker. The control unit 19 controls the pulse generator 9 via a control line 20 so that the pulse repetition rate of the pacing pulses is correspondingly shifted from a lower pacing rate toward higher pacing rates with an increasing frequency of the respiration signal at the output of the difference former 18. The pacing frequency is thus appropriately adapted to the increasing requirements of the pacemaker user in a simple manner.

Although modifications and changes may be suggested by those skilled in the art it is the intention of the inventors to embody within the patent warranted hereon all changes and modifications as reasonably and properly come within the scope of their contribution to the art.

We claim as our invention:

1. A heart pacemaker comprising:
   pulse generator means for generating heart pacing pulses;
   means for acquiring a heart action signal from said heart having amplitude fluctuations therein which vary according to respiratory activity of the pacemaker user;
   respiration signal measuring means for measuring said amplitude fluctuations and generating a respiration signal therefrom; and
   control means connected to said pulse generator means and to said respiration signal measuring means for changing the rate of said heart pacing signals generated by said pulse generator means in response to said respiration signal.

2. A heart pacemaker as claimed in claim 1, wherein said respiration signal measuring means comprises a first peak value sensor for sensing positive fluctuations and a second peak value sensor for sensing negative fluctuations in said heart action signal, a difference former connected to the outputs of said first and second peak value sensors, said difference former measuring the distance between positive and negative peaks in said heart action signal, and said difference former being connected to said control unit for supplying a signal corresponding to said difference to said control unit as said respiration signal.

3. A heart pacemaker comprising: a pulse generator for generating pacing pulses for pacing a heart;
- a heart action signal detector for acquiring successive heart action signals which fluctuate positively and negatively corresponding to respiratory activity of the pacemaker user;
- means connecting said pulse generator and said heart action detector to said heart;
- a first sample/hold circuit having an input connected to said heart action detector for measuring positive peaks of said heart action signals;
- a second sample/hold circuit having an input connected to an output of said heart action detector for measuring negative peaks of said heart action signals;
- a difference former having an input to which the outputs of said first and second sample/hold circuits are supplied, said difference former generating a respiration signal as an output which corresponds to the difference between the positive and negative peaks measured by said first and second sample/hold circuits; and
- a control unit having an input connected to said difference former for receiving said respiration signal therefrom and an output connected to said pulse generator for controlling said pulse generator in dependence upon said respiration signal.

4. A heart pacemaker as claimed in claim 3, further comprising a multiplexer controlled by said control unit interconnected between said outputs of said first and second sample/hold circuits and the input of said difference former for alternatingly supplying the outputs of said first and sample/hold circuits to said input of said difference former.

5. A heart pacemaker as claimed in claim 4, further comprising an analog-to-digial converter interconnected between said multiplexer and said difference former.

* * * * *